(12) United States Patent
Liberman et al.

(10) Patent No.: US 7,415,832 B2
(45) Date of Patent: Aug. 26, 2008

(54) METHOD OF FREEZING WITH BRINE

(75) Inventors: Barnet L. Liberman, New York, NY (US); Peter H. Glidden, Sr., Windsor, CT (US); Kevin C. Vandervoort, Suffield, CT (US); Robert J. Peacock, II, Lubec, ME (US)

(73) Assignee: Winterlab Limited, New York, NY (US)

( * ) Notice: Subject to any disclaimer, the term of this patent is extended or adjusted under 35 U.S.C. 154(b) by 946 days.

(21) Appl. No.: 10/938,081

(22) Filed: Sep. 10, 2004

(65) Prior Publication Data
US 2005/0089837 A1 Apr. 28, 2005

Related U.S. Application Data

(60) Provisional application No. 60/515,324, filed on Oct. 29, 2003, provisional application No. 60/509,150, filed on Oct. 7, 2003.

(51) Int. Cl.
*F25D 17/02* (2006.01)

(52) U.S. Cl. .................... 62/64; 62/125; 62/373
(58) Field of Classification Search .............. 62/64, 62/125, 129, 373, 376
See application file for complete search history.

(56) References Cited

U.S. PATENT DOCUMENTS

| | | | | | |
|---|---|---|---|---|---|
| 2,137,902 | A | * | 11/1938 | Walter | 62/64 |
| 4,380,908 | A | * | 4/1983 | Crabb, Jr. | 62/64 |
| 4,601,909 | A | | 7/1986 | Nagoshi | |
| 4,654,217 | A | | 3/1987 | Nagoshi | |
| 4,657,768 | A | | 4/1987 | Nagoshi | |
| 4,689,963 | A | | 9/1987 | Sakai | |
| 4,769,079 | A | * | 9/1988 | Clark et al. | 106/402 |
| 4,840,035 | A | * | 6/1989 | Liberman | 62/64 |
| 5,237,835 | A | * | 8/1993 | Brochier | 62/376 |
| 5,267,490 | A | * | 12/1993 | Howells | 73/863.52 |
| 5,761,913 | A | * | 6/1998 | Liberman et al. | 62/64 |

\* cited by examiner

*Primary Examiner*—William E Tapolcai
(74) *Attorney, Agent, or Firm*—Cohen Pontani Lieberman & Pavane LLP

(57) ABSTRACT

Improved brine solutions and uses thereof for uncontaminatedly and/or efficiently freezing items such as foods, and biological samples. In accordance with one embodiment, a brine solution containing a sufficient amount of dye in conferring the solution a distinctive color is used in the freezing process. In accordance with another embodiment, a brine solution containing deionized water is used for improving the freezing efficiency and/or freezing capacity.

14 Claims, 1 Drawing Sheet

METHOD OF FREEZING WITH BRINE

RELATED APPLICATIONS

This application claims priority from U.S. Provisional Patent Application No. 60/515,324 filed on Oct. 29, 2003; and U.S. Provisional Patent Application No. 60/509,150 filed on Oct. 7, 2003.

BACKGROUND OF THE INVENTION

1. Field of the Invention

The present invention relates to a brine for use in preserving various foods and biological samples without causing contamination thereto. The present invention also pertains to a method for preserving various foods and biological samples with a brine, such as by freezing, so as not to cause contamination to the preserved items by the brine.

2. Description of the Related Art

Methods of freezing food products for long time preservation or biological samples for cytological or histological examination are known and available. For example, liquid nitrogen is a conventional method for freezing food or biological samples. Nevertheless, this method is costly since the liquid nitrogen is expensive. Moreover, there may be damage to the cellular structure of the foods or biological samples, which in turn results in deterioration in the quality of the foods, or interferes with a rapid and accurate examination of cryogenically frozen tissue.

Using a cooled brine (antifreeze solution) is another conventional freezing method. Brine includes inorganic substances such as calcium chloride, and organic substances such as ethylene glycol, and propylene glycol. Furthermore, the solution prepared by mixing the above ingredients is advantageous in that greater cooling is achieved at a comparatively lower price.

For example, "A Method of Freezing Fishery Products" is known from U.S. Pat. No. 4,601,909 issued to Nagoshi on Jul. 22, 1986. This method includes the steps of preparing a brine containing rapeseed oil, propylene glycol, calcium chloride and water, cooling the brine and immersing the seafood in the cooled brine until it is frozen. This method reduces or eliminates breakdown of muscle tissue in the seafood. Hence, deterioration in quality of the frozen product is prevented or reduced.

A similar process for "Quick Freezing of Meat" is disclosed and claimed in U.S. Pat. No. 4,654,217 issued to Nagoshi on Mar. 31, 1987. The process disclosed in this later patent is similar to that disclosed in the earlier patent except that it is applicable to beef, poultry, pork and the like.

U.S. Pat. No. 4,657,768 issued to Nagoshi on Apr. 14, 1987, discloses a "Freezing Method for Perishable Foods" which includes placing a perishable food in a heat conducting container and causing the other surface of the heat conducting container to contact cooled brine or a liquefied gas. Accordingly, the perishable food is frozen quickly without immersion.

U.S. Pat. No. 4,689,963 issued to Sakai on Sep. 1, 1987, relates to a method of freezing foods. The method of Sakai is similar to the methods of Nagoshi except that a layer of brine is placed in the heat conducting container along with the perishable food. Freezing proceeds only from the portion which is in contact with the brine and the potential for the food to stick to the container is reduced.

U.S. Pat. No. 4,840,035 provides a method of freezing a tissue specimen by using a brine comprising a cruciferous oil.

None of the aforementioned patents addresses the potential problem that the chemical ingredients of the brine may enter into the package of the foods or biological samples during the freezing process, when the package develops a puncture or tear and is compromised. Thus, the brine may contaminate the frozen foods or biological samples, and causes problems such as deteriorating the quality of the foods; causing an unpleasant or undesired taste of the foods; and interfering with rapid and accurate examination of the frozen biological samples.

Accordingly, it is desirable to find a simple, convenient, and effective freezing method, which can facilitate the identification and separation of the contaminated frozen products. In addition, there is also a need to further improve the efficiency of the freezing or the freezing capacity per unit volume of brine.

SUMMARY OF THE INVENTION

It is, therefore, an object of the present invention to provide a freezing process for quickly and conveniently identifying whether during the freezing process the brine enters into the package of a frozen item such as a food or a biological sample, and thereby preventing the frozen items from being put on the market for consumers' use or sent to the laboratory for researchers' examination.

A further object of the invention is to provide a method of freezing which facilitates monitoring the freezing progress.

Still another object of the invention is to provide a method of freezing which enables the user to conveniently determine whether the composition of the brine is within the desired balance.

Still yet another object of the invention is to improve freezing efficiency or freezing capacity per unit volume of the brine.

Still other objects and advantages of the invention will in part be obvious and will in part be apparent from the specification.

Therefore, in accordance with one embodiment of the present invention, it is provided a method of freezing an item in a package by performing the steps of:

(1) freezing the packaged item by subjecting the packaged item in contact with a pre-cooled brine having a predetermined color, the package having a sufficient clarity to enable observance of the color of the packaged item from outside of the package, and with the predetermined color of the brine being distinguishable from the color of the packaged item, (2) rinsing the outer surface of the packaged item, and (3) detecting the predetermined color appearing within the package, thereby determining whether the brine enters into the package.

Subsequent to the above detecting step, those packaged items determined to be contaminated with brine may be separated out from the remaining packaged items.

Colored brine may be used in the above method. The colored brine comprises a sufficient amount of dye for producing the predetermined color in the colored brine. For example, the brine may contain about 0.00001% of the dye. Preferably, the dye is a food grade FDA approved blue dye such as Bright Dyes® Standard Blue™ liquid concentrate ("Bright Dyes®") manufactured by Kingscote Chemicals, Inc. of Ohio. More preferably, when the pre-cooled brine absorbs the heat from the packaged item during the freezing step, the color of the brine changes, thereby indicating whether the freezing is initiated, in progress, or completed. In addition, it is also preferable that the color of the colored brine varies with the composition of the brine at a given temperature. Thus, whether the composition of the brine is in compliance with a predetermined requirement can be determined in accordance with a predetermined correlation between the color and composition balance of the brine at the given temperature.

In accordance with another embodiment of the present invention, a method of freezing is provided by preparing a brine comprising deionized water, cooling the brine to a predetermined temperature, and subjecting an item to be frozen to a heat transfer relationship with the cooled brine for a period of time sufficient to freeze the item.

For example, the brine may be cooled to a temperature ranging from about −30 to about −43° C. (−22° to −46° F.), preferably from about −38.3 to about −40.5° C. to about −41° F.). The item may be subjected to the heat transfer relationship with the cooled brine by immersing the item into the brine. The item may be frozen to a temperature of about −20° C.

The brine used in the above method comprises an effective amount of deionized water. Preferably, the brine contains at least about 0.005% by weight of cruciferous oil. More preferably the brine further contains at least one of propylene glycol and calcium chloride. One particular preferable brine comprises about 0.01% rapeseed oil, about 43.18% deionized water, about 44.06% propylene glycol, and about 12.75% calcium chloride. It is also preferable that the brine comprises a dye in a sufficient amount to produce a predetermined color of the brine.

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

DETAILED DESCRIPTION OF THE PRESENTLY PREFERRED EMBODIMENTS

Figure 1:
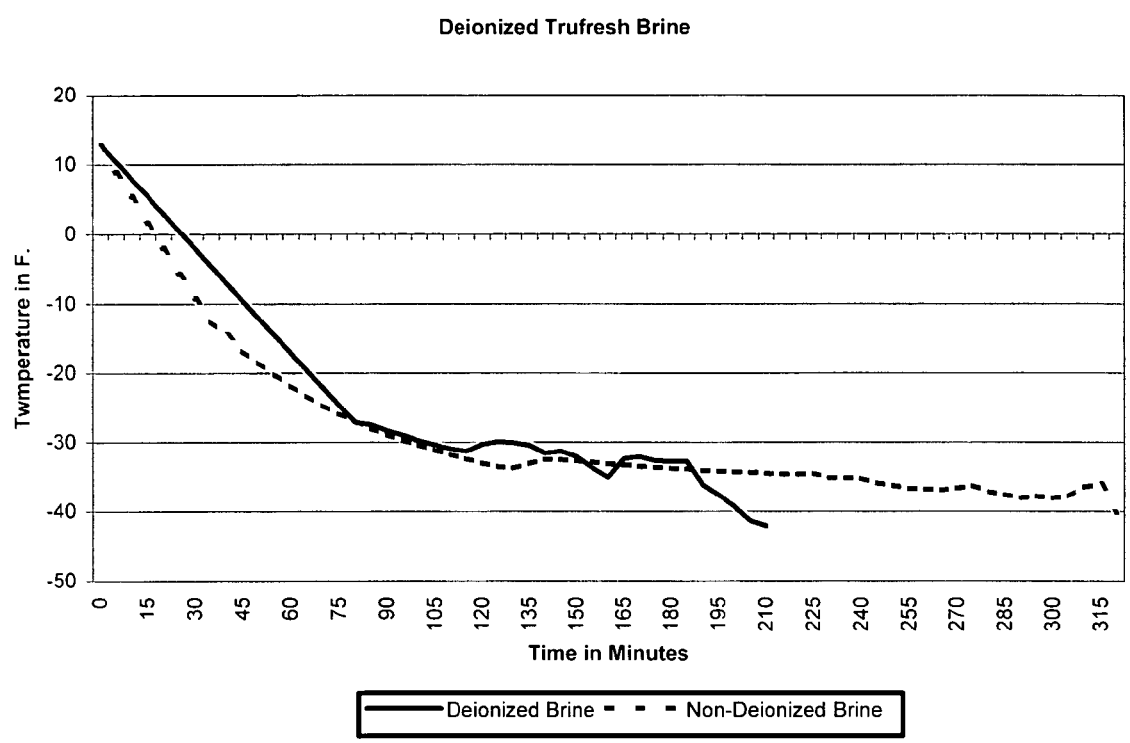
FIG. 1 illustrates the progress of cooling brine that contains deionized water to a predetermined temperature, as compared to the progress of cooling brine that contains non-deionized water to the same predetermined temperature.

As used herein, the term "an item" means anything that is suitable for being frozen with brine, which includes food and/or a biological sample. The food may be meat, seafood, vegetables, or fruit. The biological sample may be tissue, fertilized eggs, unfertilized eggs or the like.

Colored Brine

The dye used in the colored brine of the present invention can be any suitable dye, which can confer a desired color to the brine. Preferably, the dye is a food grade FDA approved dye, with a distinctive color such as blue. More preferably, the dye has a color contrasting with the color of the item to be frozen, for the convenience of identification. For observing whether the color of the brine appears inside the package, the package is preferably made of a material having a sufficient clarity, more preferably a transparent material, such as HDPE (high density polyethylene)/EVA (ethylene-vinyl acetate copolymers).

A photo cell sensitive to the color of the colored brine may be installed at the end of the washing/rinsing line connected to a solenoid driven sorter. Thus, those rinsed packages exhibiting the color of the colored brine will be detected by the photo cell, whereupon a sorting device will remove the so-detected items from the production line for disposal.

As noted above, the color of the dye preferably changes when the temperature changes, thereby enhancing the ability to determine the density of the ice crystals in the brine. One such an example is Bright Dyes® Standard Blue™. When the brine comprising such a dye is cooled to a desired level so that the brine remains in its crystal full state, the brine is in aqua marine color; when the brine is used to freeze an item, it absorbs heat from the item and visibly changes to a royal blue. Thus, the freezing progress may be observed in accordance with the color change of the brine.

The dye in the brine may also be used for determining the composition balance of the brine. For example, a color wheel guide may be devised to establish the perfect balance color at different temperatures, such as from −36.6° C. to −40.5° C. (−34° F. to −41° F.). Thus, if the color of a brine solution later used does not match the color at the corresponding temperature in the color wheel, it may indicate that the brine solution does not have the desired composition balance. Then a further full analysis of the brine solution, such as specific gravity, may need to be performed.

In addition to the dye, the colored brine of the present invention may comprise other suitable ingredients such as cruciferous oil, propylene glycol, calcium chloride and water. The colored brine may be prepared by mixing the ingredients together sequentially or concurrently. The preferred method is mixing the ingredients sequentially. For example, the colored brine may be prepared by adding the dye into a known brine solution, such as any of the brine solutions disclosed in U.S. Pat. Nos. 4,601,909; 4,654,217; 4,657,768; 4,689,963; 4,743,343; 4,840,034; 4,840,035; 5,001,047; and 6,248,381, the contents of which patents are incorporated herein by reference in their entireties.

Preferably, the colored brine comprises at least about 0.005% by weight of cruciferous oil. More preferably, about 0.005% to 0.018% by weight of cruciferous oil such as rapeseed oil should be used. Alternatively, the amount of cruciferous oil may be selected such that a maximum amount of the oil is dissolved in the brine. The dye is used in a sufficient amount to confer the desired distinctive color to the brine. For example, the amount of the dye may be 0.00001% to 0.00002% based on the total weight of the colored brine.

Presently a preferred brine composition includes, by weight, about 0.00001% dye, about 43.18% water, about 44.06% propylene glycol, about 12.75% calcium chloride, and about 0.01% rapeseed oil. The temperature of the brine should be between about −30° C. and about −43° C. (−22° F. and −46° F.), and preferably between about −38° C. and about −40° C. (−37° F. to −41° F.).

Brine Containing Deionized Water

It is now surprisingly found that using a cooled brine containing deionized water ("deionized brine") is much more efficient in freezing an item to a desired temperature such as −20° C., than using the same amount of cooled brine containing non-deionized water ("non-deionized brine") under the same conditions. In addition, it has been discovered that it takes significantly less time to cool the deionized brine itself to a predetermined temperature such as −40° C. than to cool the same amount of non-deionized brine to the same predetermined temperature.

The process of deionizing water removes as much inorganic material as possible from the water used in the mixing of the brine. Inorganic substances contaminate feed water as the water travels to its place of use. For example, calcium and magnesium (two substances that cause "hard water") dissolve into the water from the rock formations of the water's origin. Carbon dioxide gas also dissolves into the water, making it mildly acidic. Silicates leach from sandy riverbeds or from glass transport vessels, and ferrous iron also joins the solution in transit, from iron pipes. Chloride and fluoride are added at the water treatment plant. Accidental pollution occurs with nitrates from fertilizer and phosphates from detergents.

Deionization is a method used most often by laboratories to produce purified water on-demand and is able to purify water to a maximum resistivity of 18.2 megohm/cm at 25° C. Deionization may be conducted by exchanging hydrogen ions for cationic and hydroxyl ions for anionic contaminants in the feed water. For example, the deionization resins, which are tiny spherical plastic (resin) beads through which the feed water passes, may be used for producing the deionized water.

The following examples further illustrate the present invention without limiting it.

EXAMPLE 1

Example 1 was designed to detect the presence of brine that permeated the HDPE/EVA packaging.

Example 1 follows the following procedure:

a) slowly added 2.08 ml of Bright Dyes™ to 208 liters Trufresh® to make a colored brine (Trufresh® comprises about 0.01% rapeseed oil, about 43.18% water, about 44.06% propylene glycol, and about 12.75% calcium chloride);

b) cooled the colored brine to −40° C.;

c) prepared four transparent HDPE/EVA packages of fresh salmon which is bright pink;

d) intentionally compromised two of the four packages;

e) immersed the four packages in the colored brine for 18 minutes;

f) removed the four packages from the colored brine and rinsed them.

After the rinsing, blue color clearly appeared inside those two intentionally compromised package; whereas blue color appeared inside neither of the other two packages.

EXAMPLE 2

Example 2 provides a specific procedure for establishing the color chart.

The procedure comprises:

a) mix 265 liters (70 U.S. gallons) of TruFresh® brine perfectly with 2.65 ml Bright Dyes™ dye to make a colored brine with a desired composition balance;

b) place 189 liters (50 U.S. gallons) of the colored brine in a freezer;

c) prepare ten 0.946 liters (1 quart) samples of brine by respectively decreasing the water concentration of the colored brine by 2%, 6%, 10%, . . . , and 40%;

d) prepare ten 0.946 liters (1 quart) samples of brine by respectively decreasing the propylene glycol concentration of the colored brine by 2%, 4%, 6%, . . . , and 20%.

e) place samples of the off brine samples of c) and d) in a small container, open top, reduce temperature to −40° C., and stir;

f) when both good brine of b) and off brine samples of c) and d) are at the same temperature, take photos of the good brine and off brine with good overhead light.

g) make a color chart in accordance with the photos of f) showing the correlation of the color and the composition of the brine solution.

h) repeat the above, respectively, at −20° C., −22° C., . . . , −40° C., and −42° C.

The color chart thus provides a tool to show composition balance of the brine solution at different temperatures by color.

EXAMPLE 3

Example 3 illustrates that cooling a deionized brine to a predetermined temperature such as −40° C. takes a significantly shorter time than cooling non-deionized brine.

A brine tank with a full brine capacity of 37.85 liters (10 U.S. gallons) was used in the following tests.

The first test uses the deionized water according to the following procedure:

a) add 30.3 liters (8 U.S. gallons) of brine to the brine freezer; the brine contains about 43.18% deionized water, about 44.06% propylene glycol, about 12.75% calcium chloride, and about 0.01% rapeseed oil; b) cool the brine in the brine freezer to −41° C.; and c) record the temperature of brine every five minutes.

In the second test, the deionized water in the brine of the freezer was replaced with non-deionized water. Other conditions remained the same as the first test.

The results of the above two tests are listed in the following table and shown in FIG. 1.

| Cooling time (Minutes) | Test 1 Temperature of Non-deionized brine ° F. | Test 2 Temperature of deionized brine ° F. |
| --- | --- | --- |
| 0 | 70.4 | 12.9 |
| 5 | 12.7 | 10.4 |
| 10 | 8.9 | 7.9 |
| 15 | 5.4 | 5.4 |
| 20 | 1.6 | 2.9 |
| 25 | −2 | 0.4 |
| 30 | −5.7 | −2.1 |
| 35 | −9.2 | −4.6 |
| 40 | −12.5 | −7.1 |
| 45 | −14.4 | −9.6 |
| 50 | −16.7 | −12.1 |
| 55 | −18.4 | −14.6 |
| 60 | −20.1 | −17.1 |
| 65 | −21.7 | −19.6 |
| 70 | −23.2 | −22.1 |
| 75 | −24.6 | −24.6 |
| 80 | −25.8 | −27.1 |
| 85 | −26.8 | −27.4 |
| 90 | −28 | −28.3 |
| 95 | −28.9 | −29.0 |
| 100 | −29.7 | −29.8 |
| 105 | −30.4 | −30.4 |
| 110 | −31.1 | −31.0 |
| 115 | −31.8 | −31.3 |
| 120 | −32.4 | −30.3 |
| 125 | −33 | −29.9 |
| 130 | −33.5 | −30.1 |
| 135 | −33.8 | −30.5 |
| 140 | −33.1 | −31.6 |
| 145 | −32.5 | −31.3 |
| 150 | −32.5 | −32.1 |
| 155 | −32.7 | −33.7 |
| 160 | −32.9 | −35.1 |
| 165 | −33.1 | −32.4 |
| 170 | −33.3 | −32.1 |
| 175 | −33.5 | −32.7 |
| 180 | −33.6 | −32.8 |
| 185 | −33.8 | −32.8 |
| 190 | −33.9 | −36.2 |
| 195 | −34.1 | −37.7 |
| 200 | −34.2 | −39.3 |
| 205 | −34.3 | −41.4 |
| 210 | −34.4 | −42.1 |
| 215 | −34.5 | |

-continued

| Cooling time (Minutes) | Test 1 Temperature of Non-deionized brine °F. | Test 2 Temperature of deionized brine °F. |
| --- | --- | --- |
| 220 | −34.7 | |
| 225 | −34.7 | |
| 230 | −34.5 | |
| 235 | −35.2 | |
| 240 | −35.2 | |
| 245 | −35.3 | |
| 250 | −35.9 | |
| 255 | −36.3 | |
| 260 | −36.7 | |
| 265 | −36.8 | |
| 270 | −36.9 | |
| 275 | −36.7 | |
| 280 | −36.3 | |
| 285 | −37.2 | |
| 290 | −37.6 | |
| 295 | −38.1 | |
| 300 | −37.8 | |
| 305 | −38.1 | |
| 310 | −37.8 | |
| 315 | −36.5 | |
| 320 | −36.1 | |
| 325 | −40.1 | |

As shown the above table and FIG. 1, it took about 320 minutes to cool the non-deionized brine from the temperature of about +12° F. to about −40° F.; whereas it only took about 200 minutes to cool the same amount of deionized brine. If starting from about −20° F., it took about 265 minutes to cool the non-deionized brine to about −40° F.; whereas it took only about 135 minutes to cool the same amount of deionized brine to the same temperature. If starting from -about 30° F., it took about 220 minutes to cool the non-deionized brine to −40° F.; whereas it only took about 100 minutes to cool the same amount of deionized brine to −40° F. Hence, the efficiency of cooling the brine by using deionized water has been significantly improved, compared to the use of non-deionized water.

The invention is not limited by the embodiments described above which are presented as examples only but can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of freezing an item sealed in a package comprising:
    freezing the item by causing the item to contact a pre-cooled brine having a predetermined color; wherein the package exhibits a clarity enabling observance of the color of the item from outside of the package; and wherein the predetermined color of said brine is distinguishable from the color of the item;
    rinsing the outer surface of the package containing the item and
    determining whether said brine enters into the package by evaluating the color of the item through the package.

2. The method of claim 1 further comprising a step of separating a frozen packaged item with said brine inside the package, from a frozen packaged item without said brine inside the package based on the result of said determining step.

3. The method claim 1 wherein the item is selected from the group consisting of a food and a biological sample.

4. The method of claim 3 wherein the food is selected from the group consisting of meat, seafood, fruit, and vegetable.

5. The method of claim 3 wherein the biological sample is selected from the group consisting of tissue, stem cells, fertilized eggs and unfertilized eggs.

6. The method of claim 1 wherein said brine comprises at least 0.005% by weight of cruciferous oil.

7. The method of claim 1 wherein said brine comprises deionized water.

8. The method of claim 1 wherein based on the total weight of said brine, said brine comprises about 0.01% rapeseed oil, about 43.18% water, about 44.06% propylene glycol, and about 12.75% calcium chloride.

9. The method of claim 1 wherein said brine comprising a dye that produces said predetermined color.

10. The method of claim 9 wherein said dye is a food grade FDA approved blue dye.

11. The method of claim 9 wherein the color of said dye visibly changes when said brine absorbs heat from the item during said freezing step, thereby indicating whether said freezing is initiated, in progress, or completed.

12. The method of claim 11 wherein the color of said brine at a given temperature varies with the composition of said brine so that a determination can be made as to whether the composition of said brine is in compliance with a predetermined requirement, said predetermined requirement comprising a correlation between the color of said brine and the composition of said brine.

13. The method of claim 12 wherein a pre-established color wheel is made to reflect said correlation between the color and composition of said brine in a temperature ranging from −20° C. to −41° C.

14. The method of claim 1 wherein the package is made of at least one of high density polyethylene and ethylene-vinyl acetate copolymers.

* * * * *